United States Patent
Raskar et al.

(10) Patent No.: US 8,009,192 B2
(45) Date of Patent: Aug. 30, 2011

(54) SYSTEM AND METHOD FOR SENSING GEOMETRIC AND PHOTOMETRIC ATTRIBUTES OF A SCENE WITH MULTIPLEXED ILLUMINATION AND SOLID STATES OPTICAL DEVICES

(75) Inventors: Ramesh Raskar, Cambridge, MA (US); Hideaki Nii, Cambridge, MA (US); Jay W. Summet, Atlanta, GA (US); Yong Zhao, Providence, RI (US); Paul H. Dietz, Hopkinton, MA (US); Jonathan Westhues, Cambridge, MA (US); Michael Noland, Chapel Hill, NC (US); Erich Bruns, Saarburg (DE); Shree Nayar, New York, NY (US); Vlad Branzoi, Lawrenceville, NJ (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 1177 days.

(21) Appl. No.: 11/435,703

(22) Filed: May 17, 2006

(65) Prior Publication Data

US 2007/0268363 A1 Nov. 22, 2007

(51) Int. Cl.
*H04N 7/18* (2006.01)
*H04N 5/222* (2006.01)
*G02B 13/16* (2006.01)
*G06K 19/06* (2006.01)
*H04N 5/225* (2006.01)

(52) U.S. Cl. ......... 348/135; 348/335; 348/370; 235/492

(58) Field of Classification Search .................. 348/139, 348/164, 153–155, 335, 370; 235/492
See application file for complete search history.

(56) References Cited

U.S. PATENT DOCUMENTS

| 5,874,724 | A * | 2/1999 | Cato .............................. 235/492 |
| 6,333,749 | B1 * | 12/2001 | Reinhardt et al. ............. 345/629 |
| 6,630,915 | B1 * | 10/2003 | Flood ................................ 345/8 |
| 7,151,454 | B2 * | 12/2006 | Washington ............... 340/572.1 |
| 7,154,395 | B2 * | 12/2006 | Raskar et al. .............. 340/572.4 |
| 7,229,023 | B2 * | 6/2007 | Raskar .......................... 235/492 |
| 2001/0017651 | A1 * | 8/2001 | Baker et al. ................... 348/169 |
| 2004/0212725 | A1 * | 10/2004 | Raskar .......................... 348/370 |
| 2005/0002572 | A1 * | 1/2005 | Saptharishi et al. .......... 382/224 |

(Continued)

FOREIGN PATENT DOCUMENTS

GB 2410151 A * 7/2005

OTHER PUBLICATIONS

Raskar et al., "RFIG Lamps: Interacting with a Self-Describing World Via Photosensing Wireless Tags and Projectors" ACM SIGGRAPH 2004, vol. 23, No. 3, pp. 406-415.*

(Continued)

*Primary Examiner* — David Ometz
*Assistant Examiner* — Carramah J Quiett
(74) *Attorney, Agent, or Firm* — Dirk Brinkman; Gene Vinokur

(57) ABSTRACT

An optical receiver is arranged at a location in a scene. The optical receiver includes a photo sensor configured to detect spatio-temporal modulated optical signals directed at the scene from a set of spatially dispersed optical transmitters, and to convert the optical signals from each of the optical transmitters to a corresponding electronic signal. The electronic signals can be analyzed to determine geometric properties of the location in the scene.

16 Claims, 8 Drawing Sheets

U.S. PATENT DOCUMENTS

| | | | |
|---|---|---|---|
| 2005/0040241 A1* | 2/2005 | Raskar | 235/492 |
| 2005/0116821 A1* | 6/2005 | Wilsey et al. | 340/539.13 |
| 2005/0128293 A1* | 6/2005 | Wilsey et al. | 348/143 |
| 2006/0000911 A1* | 1/2006 | Stekel | 235/462.32 |
| 2006/0001543 A1* | 1/2006 | Raskar et al. | 340/572.1 |
| 2009/0009288 A1* | 1/2009 | Fogg | 340/10.1 |

OTHER PUBLICATIONS

U.S. Appl. No. 10/643,614, filed Aug. 19, 2003, Raskar.
U.S. Appl. No. 10/883,235, Jul. 1, 2004, Raskar et al.
U.S. Appl. No. 10/030,607, filed Jan. 5, 2005, Raskar.
Ringwald, "Spontaneous Interaction with Everyday Devices Using a PDA," UbiComp, 2002.
Ma and Paradiso, "The FindIT Flashlight: Responsive Tagging Based on Optically Triggered Microprocessor Wakeup," UbiComp, pp. 160-167, 2002.
Nii et al., "Smart light ultra high speed projector for spatial multiplexing optical transmission," International Workshop on Projector-Camera Systems, Jun. 25, 2005, San Diego, California, USA.
Lee et al., "Moveable interactive projected displays using projector based tracking," UIST 2005.

* cited by examiner

SYSTEM AND METHOD FOR SENSING GEOMETRIC AND PHOTOMETRIC ATTRIBUTES OF A SCENE WITH MULTIPLEXED ILLUMINATION AND SOLID STATES OPTICAL DEVICES

RELATED APPLICATIONS

This application is related to U.S. patent application Ser. No. 11/435,565, "Apparatus and Method for Illuminating a Scene with Multiplexed Illumination for Motion Capture" and U.S. patent application Ser. No. 11/435,581, "System and Method for Measuring Scene Reflectance using Optical Sensors," both of which were co-filed with this application by Raskar et al, on May 17, 2006.

FIELD OF THE INVENTION

This invention relates generally to optical sensing for motion capture, and more particularly to sensing geometric and photometric attributes of a scene using multiplexed illumination.

BACKGROUND OF THE INVENTION

A major trend in illumination is solid-state lighting that uses light emitting diodes (LEDs). As LEDs begin to replace incandescent and fluorescent lamps, LEDs can be used for multiplexed optical communication with intelligent devices in addition to providing illumination. Solid-state optical emitters are compact, can be modulated at a high data rate, and can be selected to emit light as a narrow bandwidth optical signal.

It is widely accepted that solid-state lights will soon be ubiquitous—in homes, offices and shops, Tsao, "Light emitting diodes (LEDs) for general illumination," U.S. Department of Energy Lighting Technology Roadmap, 2002; and Talbot, "LEDs vs. the lightbulb," MIT Technology Review, 2003.

Conventional scene acquisition methods use cameras to determine an interaction between geometric and photometric attributes of a scene. However, analyzing scenes using camera images is known to be a difficult inverse light transport problem, because the radiance measured at each camera pixel is a complex function of geometry, illumination, and reflectance.

Optical Communication and Demodulation

It is now possible to achieve several modulation operations on optical signals that were once only possible in the radio frequency (RF) range. Among the motivations for selecting optical communication instead of radio frequency communication are benefits such as directionality, lack of interference in RF sensitive environments, and higher bandwidths.

While a majority of the prior art solid state lighting applications are in communication for point-to-point data transfer, these concepts can be extended to free-space interaction. A remote control for a device is an example where an infrared LED is temporally modulated by binary codes at a carrier frequency of about 40 KHz. The signal is acquired by a photo sensor mounted at the front of the device and demodulated to perform various device functions.

Other systems allow incandescent lights to communicate with devices in a room, Komine and Nakagawa, "Fundamental analysis for visible-light communication system using LED lights," IEEE Transactions on Consumer Electronics, vol. 50, no. 1, pp. 100-107, 2004. Vehicle tail-lights can continuously transmit speed and braking conditions in a narrow direction to following vehicles, Misener et al., "Sensor-friendly freeways: Investigation of progressive roadway changes to facilitate deployment of AHS," Tech. Rep. UCB-ITS-PRR-2001-31, 2001.

Location Tracking

Several techniques for motion tracking using magnetic, acoustic, optical, inertial, or RF signals are available, Welch and Foxlin, "Motion tracking: No silver bullet, but a respectable arsenal," IEEE Comput. Graph. Appl., vol. 22, no. 6, pp. 24-38, 2002.

Typically, optical systems have shorter latencies and provide greater accuracy. In addition, an optical channel can be exploited to investigate the photometric aspect of scene capture.

Most motion capture systems used in movie studios employ high-speed cameras to observe passive visible markers or active LED markers. For example, a high-speed digital video camera can record 1280×1024 full-frame grayscale pixels at speeds of up to 484 frames per second with onboard processing to detect the marker position. Those devices provide highly reliable output data. However, the extremely expensive high-speed cameras pose several issues in terms of scalability. Bandwidth limits the resolution as well as the frame-rate. Higher frame-rates demand shorter exposure time. That requires bright controlled scene lights for the passive markers or the use of battery operated LED markers. To segment the markers from the background, those systems also use methods for increasing marker contrast. That usually requires that the actor wears dark clothes in a controlled lighting situation. It is desired to perform motion capture in natural settings.

Photo Sensing

A number of systems are known for locating objects having attached photo sensors, Ringwald, "Spontaneous Interaction with Everyday Devices Using a PDA," Workshop on Supporting Spontaneous Interaction in Ubiquitous Computing Settings, UbiComp, 2002; Patel and Abowd, "A 2-Way Laser-Assisted Selection Scheme for Handhelds in a Physical Environment," UbiComp, pp. 200-207, 2003; and Ma and Paradiso, "The FindIT Flashlight: Responsive Tagging Based on Optically Triggered Microprocessor Wakeup," UbiComp, pp. 160-167, 2002.

Other systems locate photo sensing RFID tags with a conventional digital projector, Nii et al., "Smart light ultra high speed projector for spatial multiplexing optical transmission," International Workshop on Projector-Camera Systems, Jun. 25, 2005, San Diego, Calif., USA; Raskar et al., "RFIG lamps: Interacting with a self-describing world via photo-sensing wireless tags and projectors," ACM Transactions on Graphics vol. 23, no. 3, pp. 406-415, 2004; Lee et al., "Moveable interactive projected displays using projector based tracking," UIST 2005: Proceedings of the 18th annual ACM symposium on user interface software and technology, ACM Press, New York, N.Y., USA, pp. 63-72, 2005; and U.S. patent application Ser. No. 10/643,614 "Radio and Optical Identification Tags" filed by Raskar on Aug. 19, 2003, Ser. No. 10/883,235 "Interactive Wireless Tag Location and Identification System" filed by Raskar et al. on Jul. 1, 2004, and Ser. No. 10/030,607 "Radio and Optical Identification Tags" filed by Raskar on Jan. 5, 2005 all incorporated herein by reference.

The UNC "HiBall" system uses a group of six rigidly fixed position sensitive detectors (PSD) to find location and orientation with respect to actively blinking LEDs, see Welch, "Scaat: Incremental tracking with incomplete information," UNC Tech. Report, Chapel Hill, N.C., USA, 1886. Each LED provides a single under-constrained reading at a time. That system requires a large ceiling installation, and active control of the LEDs operating in an open loop.

Systems such as "Indoor GPS" use low-cost photo sensors and two or more rotating light sources mounted in the environment, Kang and Tesar, "Indoor GPS metrology system with 3d probe for precision applications, Kang, S. and Tesar, D., "A Noble 6-DOF Measurement Tool With Indoor GPS For Metrology and Calibration of Modular Reconfigurable Robots," IEEE ICM International Conference on Mechatronics, Istanbul, Turkey, 2004. The rotating light sources sweep out distinct planes of light that periodically illuminate the photo sensors. That system operates at a rate of 60 Hz.

Factoring Reflectance and Illumination

Scene Factorization

Scene factorization, as defined herein, is a computer vision technique for inferring scene parameters. The scene parameters can include geometry and photometry. The geometry defines the 3D locations, orientations, and shapes of objects in the scene, and the photometry defines the interaction of light with the objects. The light can be due to direct illumination, reflectance, radiance, and translucency, see generally, C. Tomasi and T. Kanade, "Shape and Motion from Image Streams: A Factorization Method," Proceedings of the National Academy of Sciences, vol. 90, pp. 995-9802, 1993.

Camera-based factorization of scene radiance into a product of incident illumination and albedo is known in computer vision applications. The problem formulation can involve multiple views, a single view with variable illumination, or both, Forsyth and Ponce, "Computer Vision, A Modem Approach," 2002.

However, scene factorization is an ill-posed problem and solutions require assumptions regarding the reflectance variation in the scene and/or the illumination variation due to the light source.

Communication with Optical Tags

The use of spatio-temporal optical modulation is influenced by developments in radio frequency, available bandwidth in optical communication, and opportunities in projective geometry. In light based communication, the optical bandwidth, which is a product of temporal and spatial bandwidth, has been increasing annually by about a factor of three. The penetration of solid state LEDs in diverse fields, such as optical networking, CD readers, and IrDA, indicates a trend in versatile temporal modulation of light sources. At the same time, high resolution spatial modulation is becoming possible via microelectromechanical (MEMS) based, liquid crystal on silicon (LCOS), grating light valve (GLV) and traditional liquid crystal display (LCD) imagers.

Optical Communication Tools

A range of optical emitter and receiver devices are available for use in an optical scene capture systems. Typically, there is a tradeoff in complexity of the emitter, the receiver and bandwidth. It is difficult to achieve high-speed scene capture with low-cost, simple devices.

It is well known that a limited dynamic range is best utilized through time-division multiplexing, followed by frequency- and code-division multiplexing (FDM and CDM), Azizoglu et al., "Optical cdma via temporal codes," IEEE Transactions on Communications, vol. 40, no. 7, pp. 1162-1170, 1992.

Therefore, it is desired to factorize scenes using low-cost solid state light emitters and sensors.

SUMMARY OF THE INVENTION

Rapid advances in solid state lighting and sensing have made possible the exploration of new scene capture techniques for computer graphics and computer vision. The high speed and accuracy of recently developed light emitters and photo sensors enable very fast and accurate attribute measurement even for highly dynamic scenes.

The embodiments of the invention combine the principles of optical data communication and the capture of scene appearance using simple, solid state optical devices. Light emitting diodes (LEDs) with a passive binary mask are used as optical emitters, and photo sensors are used as optical receivers in small optical The embodiments of the invention enable the estimation of geometric and photometric attributes of selected locations in a scene with high speed and high accuracy by strategically placing a set of optical emitters to spatio-temporally encode the 3D scene of interest. The encoding is designed by exploiting an epipolar geometric relationship between the optical emitters and receivers.

Photo sensors in optical tags, arranged at scene locations, demultiplex encoded optical signals from multiple optical emitters. Thus, the 3D location and 3D orientation of the tags, i.e., their 6D pose, can be determined. In addition, incident illumination and the reflectance of the surfaces of objects to which the tags are attached can also be measured. The measured reflectance can be used to set camera parameters, such as focus and exposure.

The embodiments of the invention can be used to enhance images, for example videos, of a scene in a way that is not possible with conventional computer vision techniques that rely only on camera images.

DETAILED DESCRIPTION OF THE PREFERRED EMBODIMENT

System and Method Overview

Figure 1:
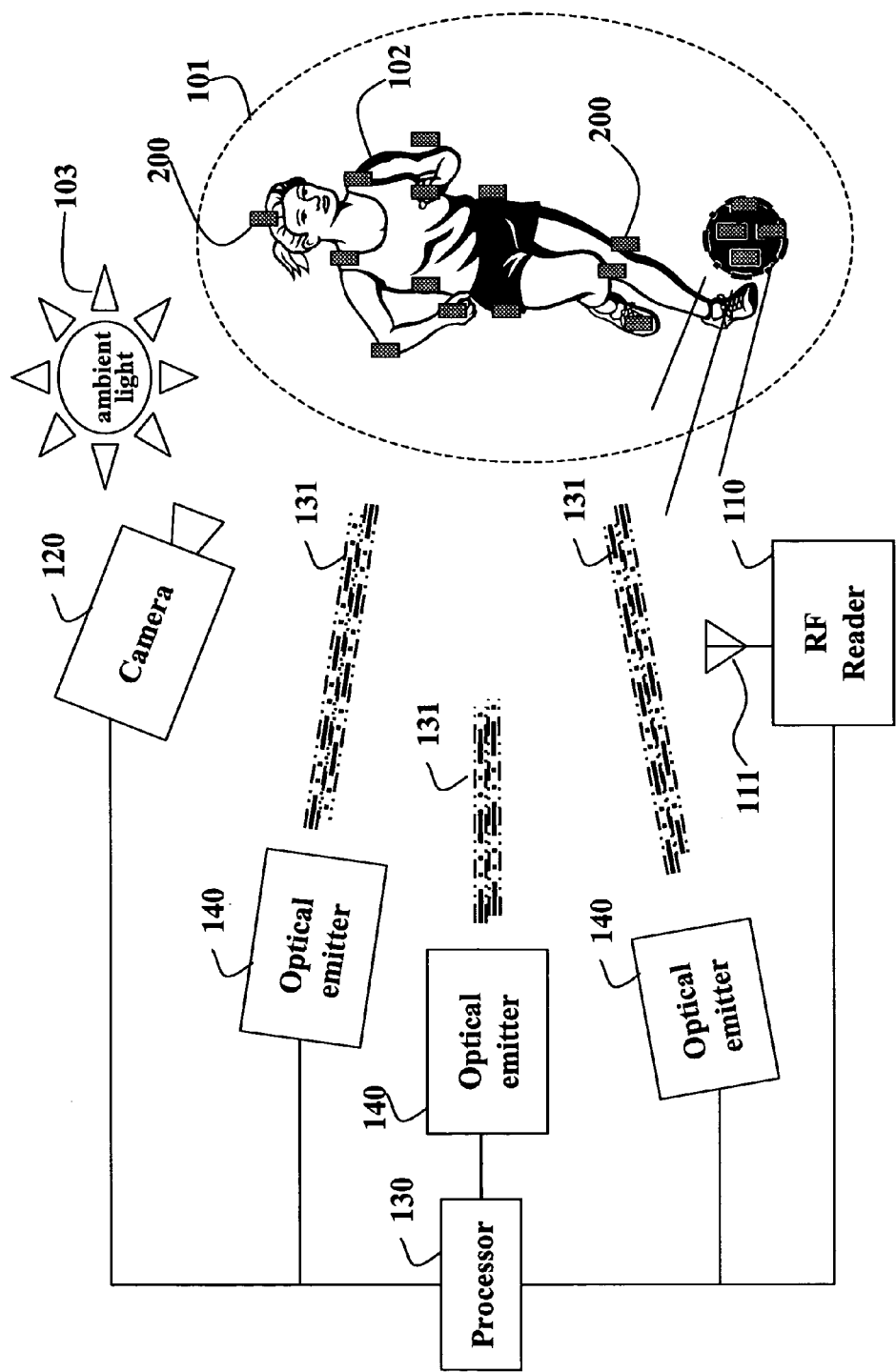
FIG. 1 is a block diagram of a system and method for factorizing a scene according to an embodiment of the invention.

FIG. 1 shows a system and method for factorizing a scene 101 according to one embodiment of our invention. The system can include one or more optical tags 200 arranged in a scene 101. The tags can be mounted on a moving object 102 or static objects, not shown. The system also includes optical emitters 140. Optionally, the system can also include a radio frequency (RF) reader 110 with an antenna 111, and a camera 120 all connected to a processor 130. The optical emitters are in the form of light emitting diodes that emit spatio-temporally modulated infrared light 131.

The scene 101 can be illuminated by ambient lighting 103, indoor or outdoor. However, it is important to note that, unlike conventional camera based tracking, the invention can also operate in the dark because infrared light is used to illuminate the tags 200. Because a camera is not used to locate the tags as in conventional computer vision systems, challenging ambient light conditions or a lack of contrast with the background is not a problem. The tags can be tracked, and the scene can be acquired in bright light as well as in complete darkness.

By strategically arranging the tags 200 and the optical emitters 140, it is possible to use light modulation and demodulation techniques to estimate individual scene attributes at locations of the tags. Although optical sensing is at a sparse set of scene locations, the richness of the sensing enables extrapolation within a small neighborhood of the tags. These measured scene attributes can therefore be used to factorize images, e.g., a video or sequence of frames, acquired by the camera 120, and to manipulate the images based on the factored attributes.

In addition, the factorization can be accomplished at a very high speed, much faster than is possible with a conventional camera based factorization. Thus, individual images can be manipulated at an intra-image level. All this is done using strikingly simple and cheap hardware components.

We describe an economical and scalable system where the optical emitters 140 are configured as space-labeling light 'beamers.' Each 'beamer' includes a linear array of solid state LEDs with a passive binary film or mask disposed between the emitters and a lenticular lens. A light intensity sequencing provides a temporal modulation, and the mask provides a spatial modulation. We use a linear array of such beamers, where the binary masks of individual beamers are carefully selected to exploit an epipolar geometry of the complete beamer arrangement. Each optical emitter 140 projects invisible (infrared) binary patterns thousands of times per second into the scene 101. In one embodiment of the invention, the LEDs are turned on and off one at a time.

Optical sensors in the tags 200 decode the transmitted space-dependent patterns and their intensities to enable us to determine the poses of the tags. As defined herein, the 6D 'pose' of a tag 200 specifies both its 3D location and its 3D orientation. The location and orientation data for each tag is determined hundreds of times per second. Therefore, the rate of change of the location and the orientation can also be determined.

The tags 200 in the scene 101 yield the locations and orientations of scene locations at a very high frequency. In addition, the tags can measure the incident ambient illumination 103. When the scene is imaged with the camera 120, we can factor, in real time, the radiances measured at the corresponding camera pixels into the incident illuminations and the intrinsic reflectance of the corresponding scene locations.

Because the scene 101 is optically labeled by the tags 200, the processing time requirements of the system remain constant, regardless of how many tags are arranged in the scene.

Optical Tags

Figure 2:
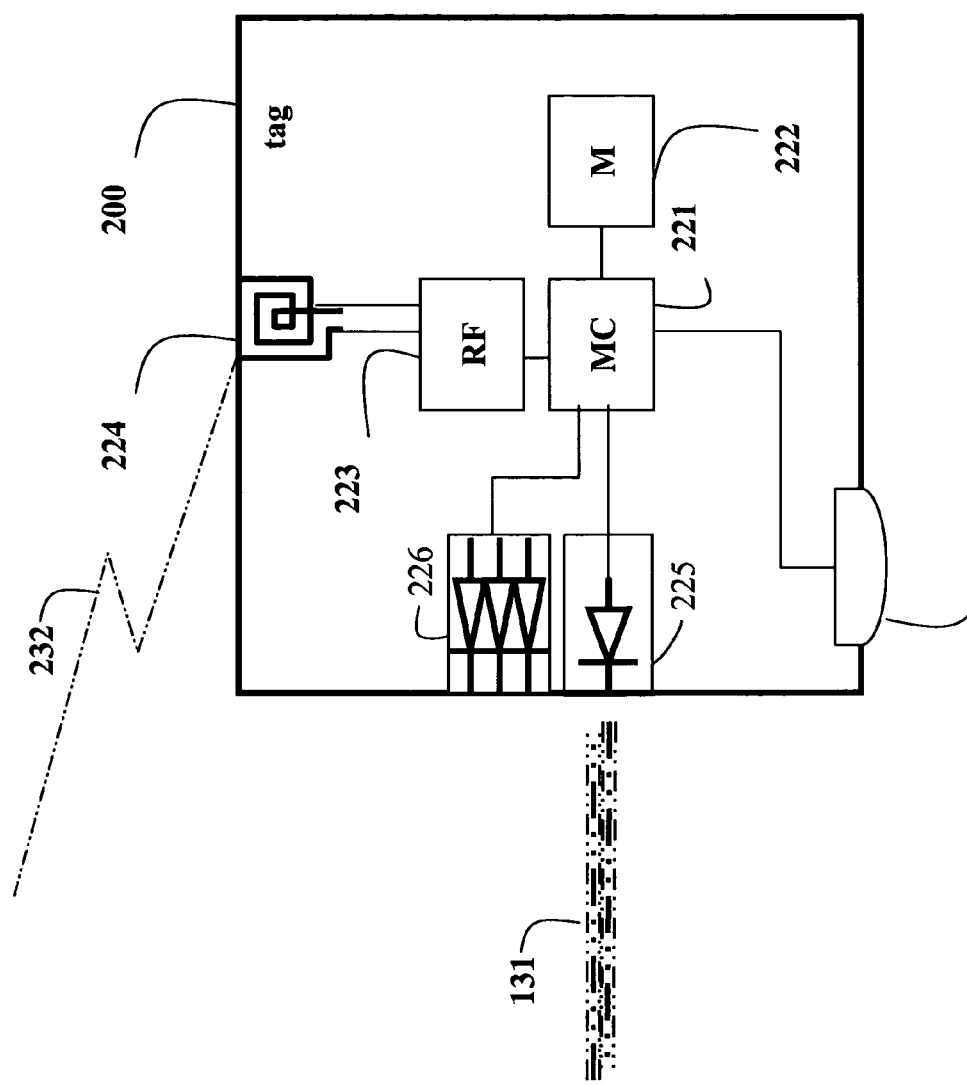
FIG. 2 is a block diagram of an optical tag according to an embodiment of the invention.

As shown in FIG. 2, each optical tag 200 includes a microcontroller (MC) 221 connected to a solid state photo sensor 225, e.g., a photodiode. The microcontroller can include a memory (M) 222, or be connected to external memory. The tag can also include RF circuitry 223 connected to a tag antenna 224. The tag antenna 224 can be in the form of a tuned induction coil, as known in the field of RFID.

The tag 200 can detect the optical signals 131 received by the photo sensor 225. The optical signals can be analyzed by software and hardware means. The hardware means can include A/D converters, comparators, timers, filters, and the like as known in the art. The software means can include instructions executed in the microcontroller 221 and data stored in the memory 222.

The tag 200 is enabled to factorize the scene 101. In contrast with the prior art, the factorization can be performed by a simple, solid state photo sensor coupled to the microcontroller, instead of cameras and complex computer systems as in the prior art.

The scene factorization, as defined herein, determines scene attributes, such as scene geometry and scene photometry. The geometry defines the 3D locations, orientations, and shapes of objects in the scene, and the photometry defines the interaction of light with the objects. The light can be due to illumination, reflectance, radiance, and translucency. In any case, the factored attributes or parameters are available as signals for further processing. The signals indicative of the scene factorization can be communicated to other devices such as the RF reader 110, or provided to an output device part 240 of the tag, e.g., indicators or displays.

By using multiple tags, a scene can be factorized by using simple, cheap, low-power components, instead of complex, expensive, high-power cameras as in the prior art. For example, the scene can be populated with hundreds of simple to install, low cost tags.

The tag reader 110, if used, can identify the tag by transmitting an RF signal to which the tag is responsive. Typically, the memory 222 of the tag stores a unique identification that can be detected when the antenna 224 of the tag couples inductively with an antenna 111 of the reader 110. This coupling changes the impedance, hence the load at the receiving antenna. The load can be modulated according to the identification code stored in the memory 222, by switching the coil 224 in and out. Similarly, the scene attribute parameters, as sensed by the photo sensor 225, can be transmitted and processed by the processor 130 by methods as described herein.

The optical emitters 140 transmit spatio-temporal modulated optical signals 131 to the tag 200. Preferably, the optical signals are in the range of infrared light, but other light wavelengths, e.g., ultraviolet, visible light, near-infrared or far-infrared, can also be used depending on scene and illumination conditions. Otherwise expressed, the wavelength of the optical signals can be in a range of about 0.01 to 1000 micrometers.

The optical signal 131 can be modulated spatially and/or temporally to carry spatial and/or temporal data. More specifically, the modulation can be amplitude, frequency, phase, polarization, time-division, code-division, or combinations thereof. In an alternative embodiment, the tag 200 can also communicate with the RF reader 110 using a RF signal 232. Unlike a camera, the photo sensor 225 is without its customary lens.

The tag 200 can decode data encoded in the optical signals 131. The tag can also determine a signal strength by low pass filtering the sensed optical signal. The tag can also measure an amount of ambient light 103, i.e., the total incident DC illumination. In one embodiment, the microcontroller 221, which can perform all of the above functions, is a Microchip PIC 16F876, Datasheet, 2004, incorporated herein by reference. The PIC 16F876 CMOS FLASH-based 8-bit microcontroller includes 256 bytes of EEPROM data memory, self programming, an ICD, two comparators, five channels of 10-bit A/D, two capture/compare/PWM functions, and a synchronous serial port.

It should be noted that semiconductor fabrication techniques can be used to manufacture tags according to embodiments of the invention as mass produced, very small scale, integrated circuits.

Figure 3:
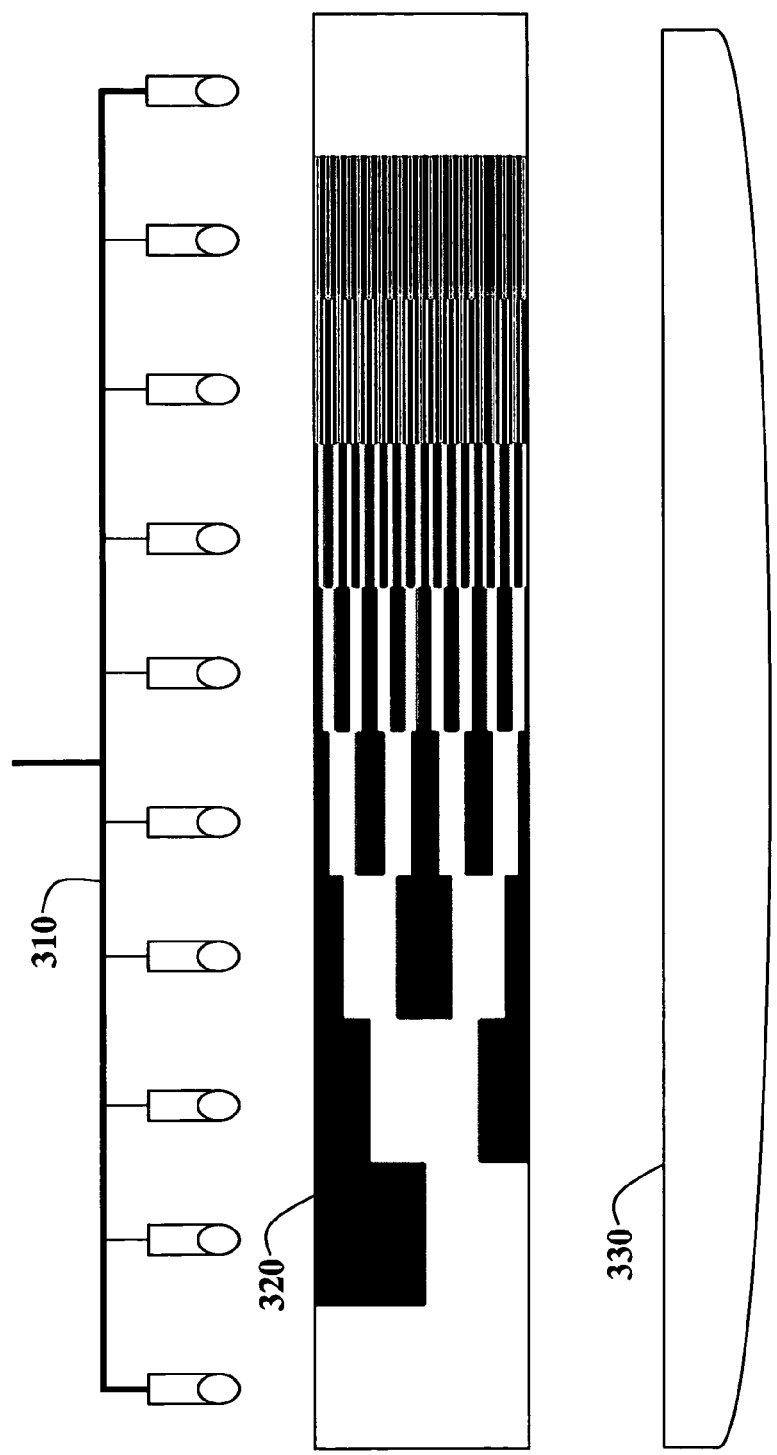
FIGS. 3 and 4 are optical emitters according to an embodiment of the invention.
Figure 4:
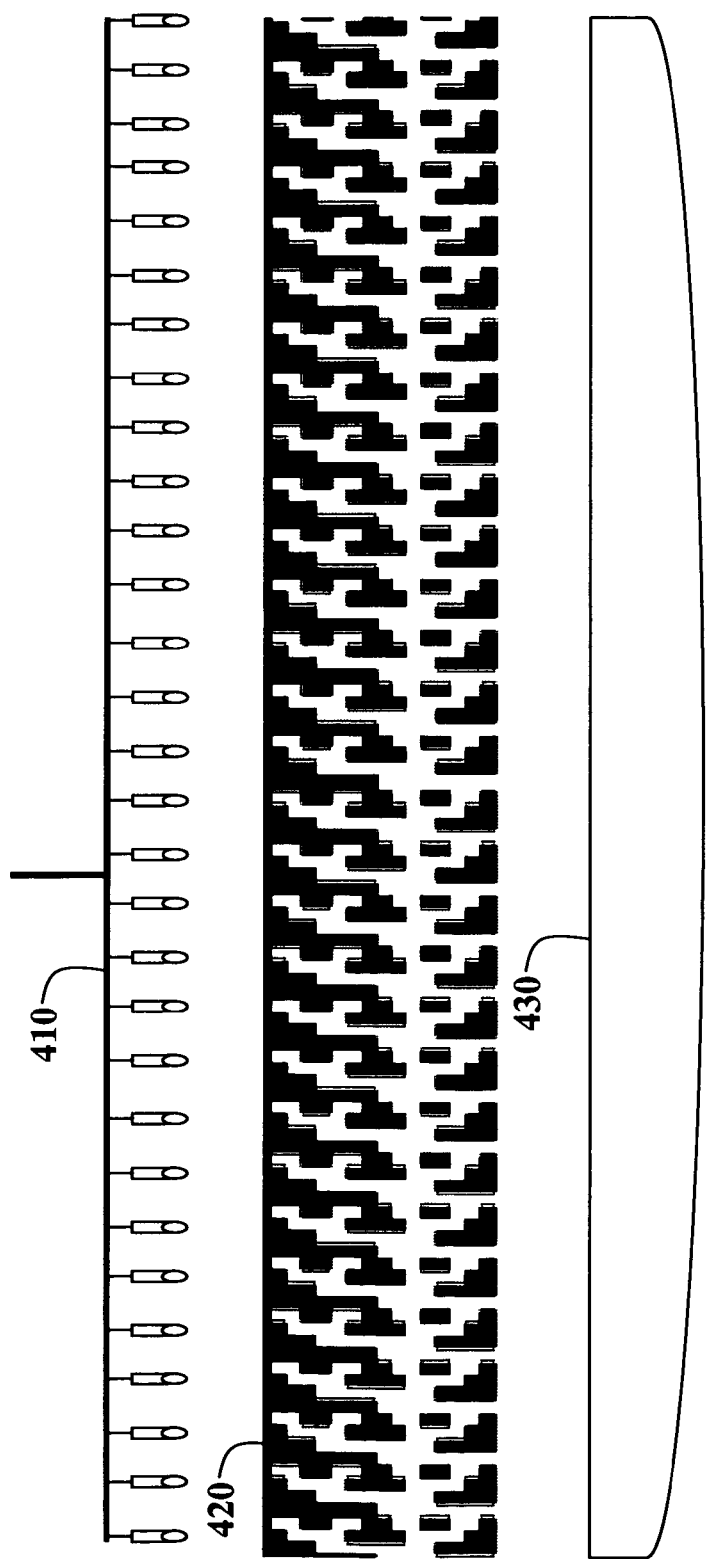

As shown in FIGS. 3 and 4, the masks 320 and 420 can be a static version of Gray coded patterns, U.S. Pat. No. 2,632,058, "Pulse code communication," issued to Gray on Mar. 17, 1953, and incorporated herein by reference. The LEDs 310 and 410 are modulated temporally in turn, at a frequency of 10,000 KHz or greater. This frequency is orders of magnitude greater than prior art detectors. This makes it possible to work with rapidly moving objects, and objects that are rotating rapidly as they move. In the prior art, such high rates can only be obtained by strobe effects.

The binary mask achieves a fixed spatial modulation. The optical signals 131 are received by the photo sensor 225 in parts where the mask is transparent and not received where the mask is opaque. Thus the LED can determine its relative horizontal and vertical position. Note, that the pattern has a one dimensional symmetry. It is possible for the mask to be in a form of a diffraction grating, a moiré pattern or a parallax barrier. The light can be projected via a mirror or a lens.

The lenticular lens 330 and 430 partitions the light source into multiple lines of light that each illuminate one 'strip' of the Gray code. By selecting the widths of each strip, all such illuminated strips are of the same pattern. By moving the light source with respect to the lenticular lens, the lines of light can be moved from one strip to another, selecting different patterns. This is achieved by having the light source be in the form of an array of LEDs, and individually modulating the LEDs.

Estimating Scene Parameters

The optical tags can determine scene parameters, such as location, surface orientation, and incident illumination. The parameters can then be used to estimate other scene attributes.

Location

The core idea in a location of a tag by sensing only a single spatial 'bit' is in exploiting an epipolar relationship, which is a fundamental geometric relationship between at least two perspective cameras, in our case the emitters 140. An epipole is a point of intersection of a line joining optical centers with the image plane. The epipole is the image in one camera of the optical centre of the other camera. An epipolar plane is a plane defined by a 3D point and the optical centers, or equivalently, by an image point and the optical centers. This family of planes is known as an epipolar pencil. An epipolar line is a straight line of intersection of the epipolar plane with the image plane. It is the image in one camera of a ray through the optical centre and image point in the other camera. All epipolar lines intersect at the epipole.

We use Gray coded patterns in a novel arrangement, as described above. Conventional Gray codes typically originate from a single projector. Our goal is to achieve binary codes, such as Gray codes, with a different code from each of the non-collocated optical emitters. In FDM or CDM techniques, all the emitters are on simultaneously.

Figure 5:
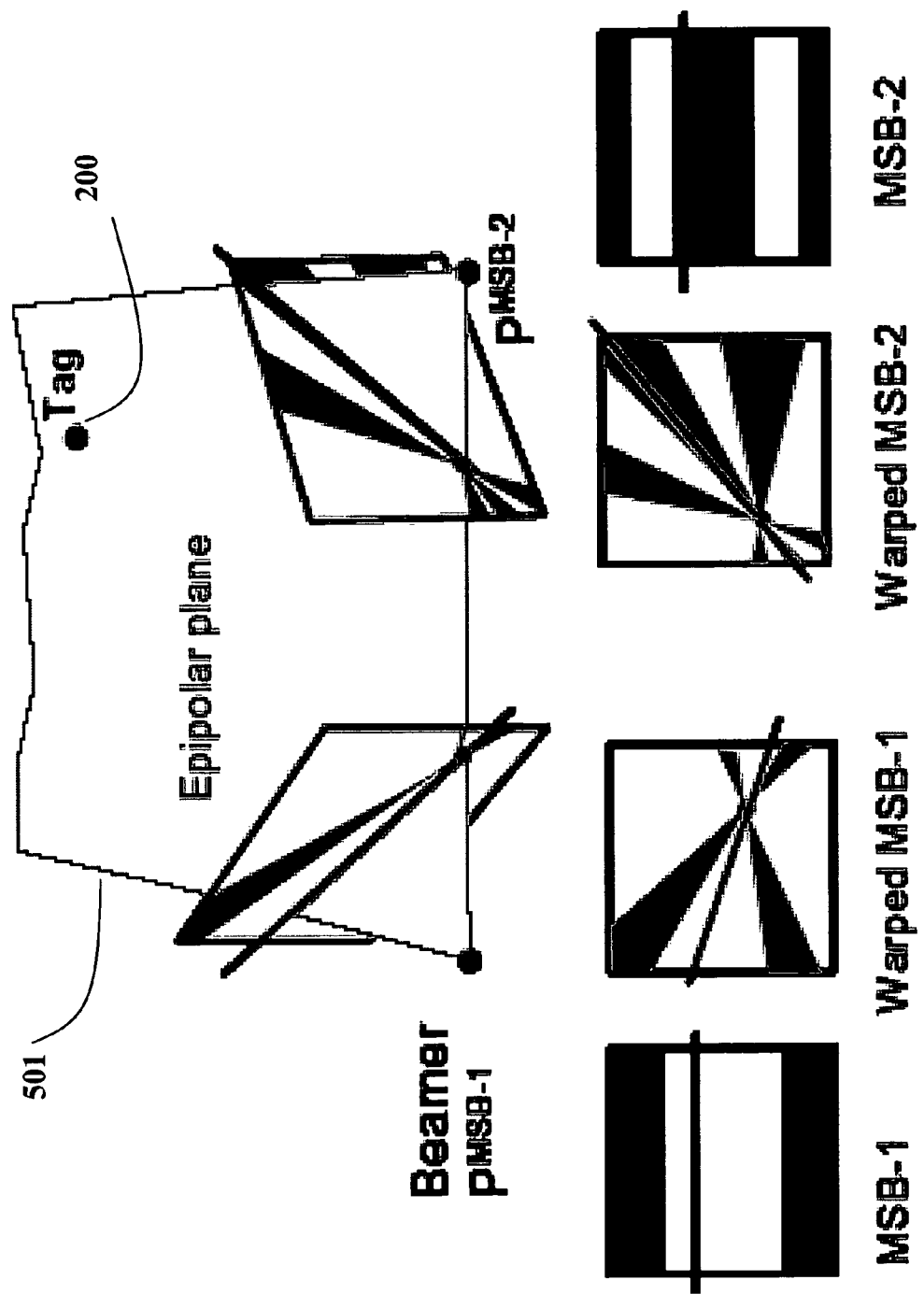
FIG. 5 is a block diagram of epipolar planes according to an embodiment of the invention.

As seen in the FIG. 5, LEDs set behind different Gray-code patterns as shown in FIGS. 3 and 4, can emit binary coded patterns that generate an appropriate 'pencil' of planes 501, if and only if the patterns are aligned along corresponding epipolar lines. The example in FIG. 5 is for two bits, e.g., MSB-1 and MSB-2.

Additional LEDs can be added to this set by ensuring that the corresponding epipolar planes 501 are identical. This is possible if a center of projection of the additional LED is collinear with the first two LEDs.

To construct a multi-bit 'projector,' we make the center of projection of all LEDs collinear. For collinear centers, the epipoles are at infinity and the corresponding epipolar lines are parallel to each other.

However, it is difficult to build N different 1-bit emitters with collinear centers of projection and align them such that the patterns share the parallel epipolar constraints. The patterns must be aligned to within the angular resolution of a least significant bit (LSB). For a ten bit code on a 10 mm-wide mask, one LSB is 10 mm. It is difficult mechanically to align the emitters to within this tolerance.

Our solution is based on observation that within a single transmitter, the pattern is constant along the direction of the epipolar line, and the pattern changes perpendicular to the epipolar lines. Hence, there is no need to use spherical lenses, which focus in both directions. Instead, we can use lenticular lenses 330 and 430 so that the lenses focus along a direction perpendicular to epipolar lines. We achieve precision by using a single lens and a single multi-pattern mask, as shown in FIGS. 3 and 4, rather than N lenses and N masks as in the prior art.

The set of N light emitters behind one common lens and mask provide a compact array for coding one dimension of the geometry. The tags decode the presence and absence of the carrier as ones and zeroes to directly measure scene coordinates. By using three or more optical emitters 140, we can determine the 3D location of the tags 200.

We have selected to exploit a geometric constraint and simplify the decoding process on the tag. The coding is optimal in the sense that we use the minimum number of bits to uniquely label the scene with optical signals.

It is also possible to use an arbitrary arrangement of individual optical emitters with masks corresponding to a random bit pattern to label the scene. This maybe sub-optimal encoding but provides greater flexibility. Given a perspective projection matrix of the N LED-emitters along with the pattern, we can determine the label by back projecting the ones and zeroes into the scene and finding the intersection.

Orientation

Conventional techniques to determine the orientation of tags include magnetic trackers or are based on integrating readings from inertial sensors. Optical solutions include position sensitive detectors (PSD), see Welch above. However, that technique requires a large form factor due to a lens used in the system.

Another sensor detects an angle of incidence by differentially processing an output current of dual photodiodes. However, that sensor can detect tilt in only one known dimension. It is also possible to estimate tag orientation by sensing the relative location of three or more sensors rigidly mounted on the tag. However, this becomes unreliable as the distance between the sensors approaches resolvable location resolution.

One embodiment of the invention estimates an instantaneous orientation of the tag 200 by exploiting a natural cosine falloff due to foreshortening and employing the known instantaneous location estimation.

Figure 6:
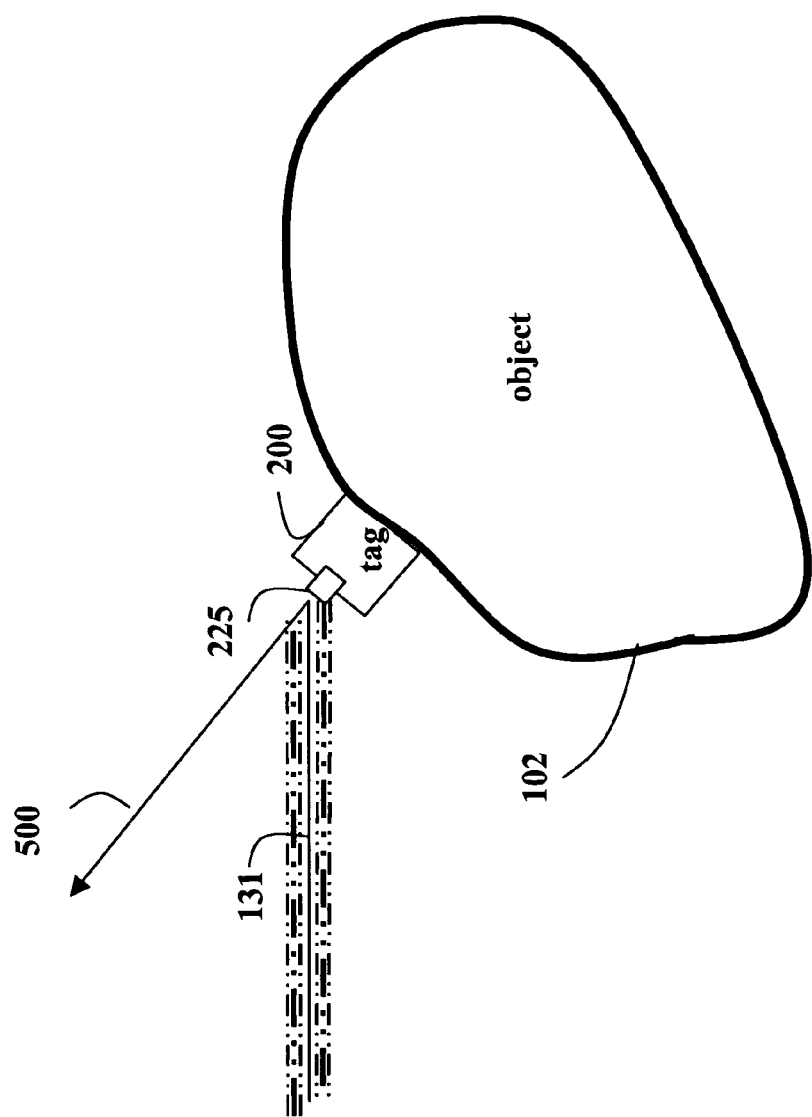
FIG. 6 is a block diagram of a tag according to an embodiment of the invention attached to an object.
Figure 8:
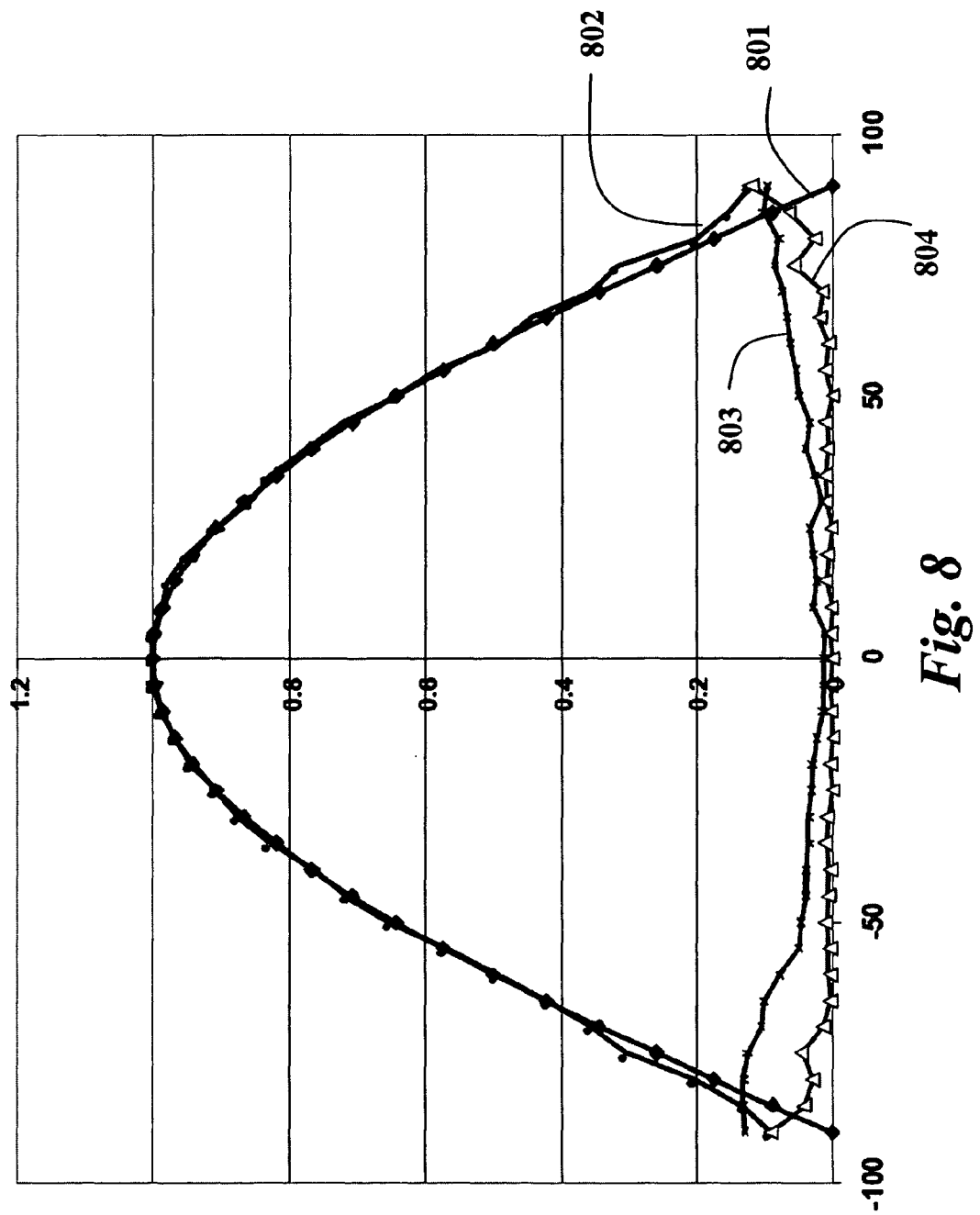
FIG. 8 is a graph of cosine fall off according to an embodiment of the invention.

As shown in FIG. 6, we assume the tag 200 with the photo sensor 225, without a lens, is attached to the surface of the object 102. We determine the surface normal 500, i.e., orientation, up to two degrees of freedom. Incident angles between incident rays from distinct light sources and the surface normal 500 attenuate the received signal intensities at the photo sensor 225 by a cosine falloff factor. When the sensor's diode is tilted, the resulting electronic signal, such as photo current or intensity (0 to 1.2) has a cosine falloff as a function angle (−100° to +100°), as shown in FIG. 8, where the ideal, measured, mean error from the ideal, and variance in error are curves 801-804 respectively.

By measuring light intensities at the tag 200 from multiple optical emitters 140 with known locations and intensities, we can determine the surface normal 500 associated with the tag 200.

We measure multiple values at a single moving tag to achieve self-calibration, i.e., we concurrently estimate a relative brightness of the emitters and the tag orientation. The intensity due to a minimum of three light sources measured at three or more distinct locations is used. Then, we can unambiguously determine the orientation of the tag with respect to each of the emitters.

Note that this problem differs from using trilateration to determine locations using a set of received signal strengths. We estimate the intensities of l light sources by moving a tag to m locations. At each tag location, we have two unknowns for orientation, and hence, we have l+2m unknowns.

At each of the m locations, we have l readings, and hence l×m equations. Because, l×m>l+2m for l≧3 and m≧l/(l−2), it follows that we need a minimum of three light sources and three tag positions.

Figure 7:
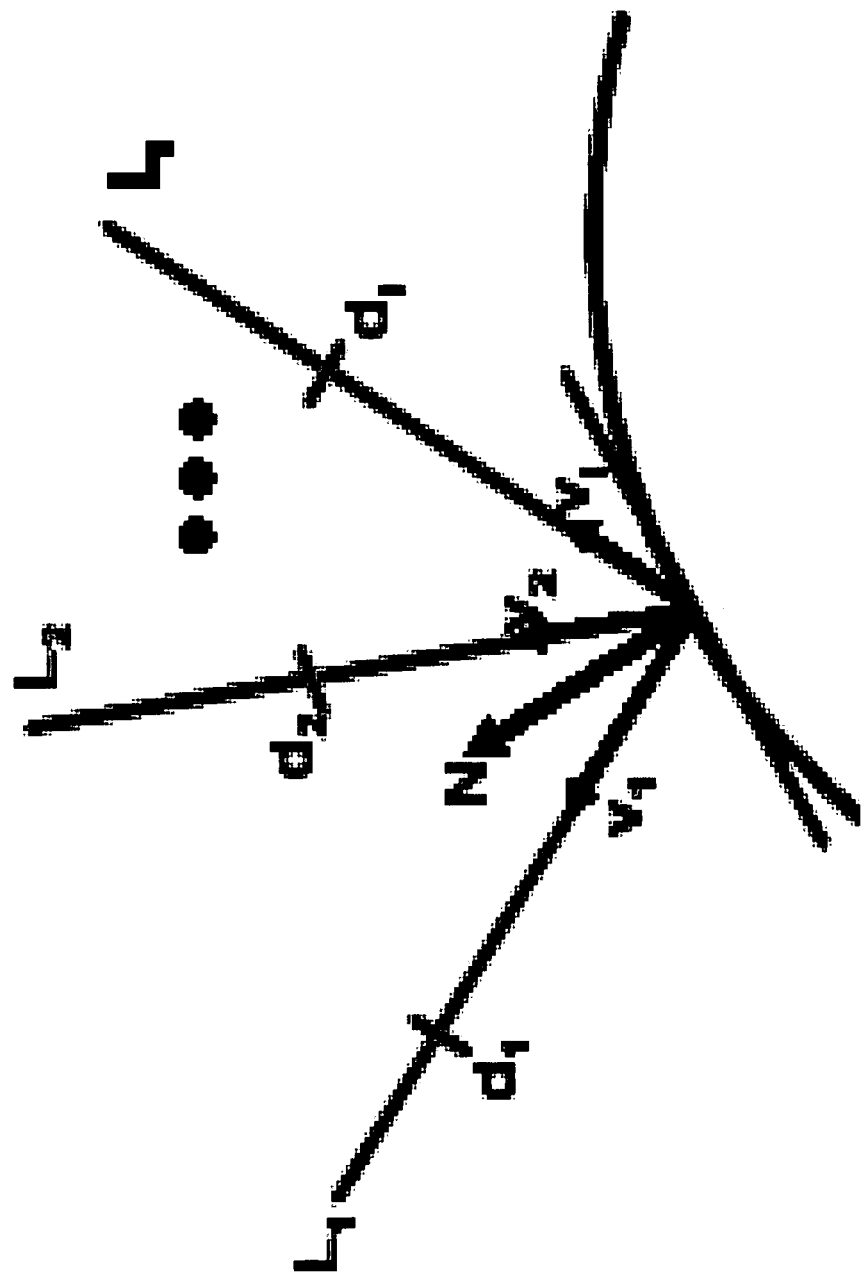
FIG. 7 is a schematic of light intensities at a surface of an object.

As shown in FIG. 7, consider $L_i$ light sources, e.g., $L_1$ and $L_2$, with intensities or power $P_i$, not shown, and where normal vectors from the tag to the sources are $V_i=[V_i x, V_i y, V_i z]$, normalized with the distance $d_i$ between the tag and the light source.

We can estimate the normal N using the intensities $I_i$ measured for the $i^{th}$ light source as $$I_i = k \cdot (V_i \cdot N)(P_i/d_i^2),$$

where k is an unknown gain of the sensor. Substituting, $Q_i = I_i d_i^2/kP_i$, and $$V = \begin{bmatrix} V_1 \\ \vdots \\ V_l \end{bmatrix}$$

$$N = \begin{bmatrix} n_x \\ n_y \\ n_z \end{bmatrix}$$

$$b = \begin{bmatrix} Q_1 \\ \vdots \\ Q_l \end{bmatrix},$$

we have, $V \cdot N = b$, and, $N = V^+ b$, where $V^+$ is the pseudo-inverse of V.

Because $|N|^2=1$, we have $N^T N=1$, i.e., $b^T V^{+T} V^+ b=1$, where T is a vector transpose operator.

We substitute, $V^{+T} V^+ = C$, so that, for each location j of the tag, we have the quadratic constraint on the unknown light source powers, $b^T C^j b = 1$.

From three or more locations, we can estimate $Q_i$, using a nonlinear optimization. We restate the quadratic constraint in terms of $C_2^{l+1}=(l(l+1)=2)$, scalars $c_i$ from the l×l symmetric matrix C.

In practice, we use six or more locations. We estimate the quadratic terms and employ the estimated intensities as an initial estimate for non-linear optimization. After the intensities are known, the tag orientation estimation is a linear process. More light sources improve the estimate at a cost of reducing the frame rate. In practice, four light sources are sufficiently reliable. Typically, we perform the self-calibration once at the beginning.

Illumination

In a preferred embodiment, we measure the optical flux arriving at the photo sensor 225 using the photo current, which is a measure of an ambient irradiance multiplied by a sensor area. The ambient flux is measured in the visible range, and hence, it is not affected by near-IR emissions. Because the area of the detector is fixed, the photo current is proportional to an integration of the irradiance over a hemisphere.

One can use a temporal low pass filtered version of the optical signal to estimate the ambient illumination because the ambient illumination is temporally smooth compared to the modulating signal. To sense color, we can use a separate triplet of closely placed sensors 226, tuned for red, green and blue wavelengths, as shown in FIG. 2.

If cross-sectional area of each photo sensor is dA, a photo current for a given irradiance E is given by a product of incident light radiance multiplied by the cosine of the angle ω between a light vector L and a tag normal N, integrated over a hemisphere W.

$$\text{Photocurrent} \propto dA \times E = dA \int_\Omega P_i(N \cdot L_i) \, d\omega_i.$$

Note that irradiance integrated over the whole hemisphere includes direct as well as global illumination.

Reflectance

A common problem in photometry is factoring radiance measured at a camera sensor into illumination and surface reflectance. This is an inverse ill-posed problem. However, given the estimates of location, surface orientation, and incident irradiance, as described above, we can determine the reflectance of the scene location if we also sample the reflected radiance using the camera 120.

The radiance B is related to the irradiance and a Lambertian reflectance ρ. Because, $B \propto E\rho$, for each wavelength λ, we have $\rho_\lambda \propto B_\lambda/E_\lambda \propto (\text{CameraPixelValue}_\lambda/\Gamma(\text{SensorPhotocurrent}_\lambda/dA))$, where $\Gamma(.)$ is the color transform function matching the RGB sensor reading to the camera colors and A is an approximate cross-sectional area of the sensor.

Thus, the surface albedo determination is greatly simplified. The albedo is estimated up to an unknown scale by taking the ratio of the camera pixel intensities values and RGB sensor values at the tag. The physical sampling means the irradiance is known at specific locations and the albedo computation is valid at the tag. We determine intrinsic reflectance for pixels around the tag sensor assuming a low frequency ambient illumination. However, the instantaneous photocurrent is noisy. Therefore, we exploit the fact that the scene location is visible over several camera frames under varying location, orientation, and illumination values, and take a weighted average to get a more accurate estimate of the true reflectance.

Before the division, we perform geometric and photometric calibration. Unlike conventional systems, the camera does not directly 'see' the tag, which is quite small. Hence, we determine Euclidean calibration between the world coordinates, the light source coordinates and the camera coordinates. Given the source coordinates, we triangulate to determine the tag location in 3D, then use a camera perspective projection matrix to estimate the 2D pixel location in the camera images. We also determine the color transform function $\Gamma(.)$ to match the color response of the camera and the RGB sensors on the tag via a color chart.

To verify our method, we estimate the intrinsic reflectance of a color chart under varying illumination, orientation, and location values. The ratio of color pixel intensities and RGB sensor values transformed via $\Gamma(.)$ remains nearly constant, and the standard deviation is under 7% of the mean value.

Applications

The above described embodiments of the invention can be used in a number of applications.

Tracking

Tags can be placed on a moving object to track the object directly, or to enhance the tracking of the object in a video acquired of the object.

Deblurring

The tags can acquire geometric data at a much higher rate than the frame rate of conventional cameras. We can use this higher temporal resolution information in various ways. For example, we attach a tag to a fast moving object and determine a point spread function (PSF) based on the geometric information. Deblurring is an ill-posed problem. However, if the PSF is accurately known, some spatial frequencies of the original signal can be recovered. High speed acquisition of incident illumination can be similarly used for recovering temporally aliased scene attributes.

Capturing Higher Dimensional Reflectance

By simply moving a surface patch in our system, an estimate of a bidirectional reflectance distribution function (BRDF) of that patch is possible. The BRDF for a given incident and exit direction is the ratio of irradiance and radiance in the corresponding directions. In every camera frame, we get a direct estimate of scene irradiance and radiance. A single fixed illumination source, a fixed camera, a fixed scene location but varying surface orientation produces a 2D slice of the 4D reflectance function. By varying the position of the scene location, several 2D slices can be recovered. Because we know the irradiance, this tag-based procedure is more accurate than a pure camera-based measurement. In addition, all the data is automatically annotated with location and identification allowing BRDF capture of a non-homogeneous reflectance surface.

Capturing Participating Media

In addition to photometric attributes of scene locations, our system can also estimate attributes of a participating media such as fog. Two or more sensors can be positioned in the environment to measure the attenuation due to the participating media. Conventional systems measure only local attenuation, e.g., practical visibility distance at an airport. In our case, the location computation system works as is, and by measuring the attenuation of the same source at two or more distinct tag locations, one can find the factor of attenuation. Because the tags are lightweight with no need for power intensive LEDs, they could be passively implemented allowing batteryless operation via a RF reader at close range. Possible uses of such tags can include fluid capture.

Illumination Manipulation

The intensity, color, or configuration of illuminators can be changed dynamically based on feedback from the tags. Photographers and videographers typically take a light meter reading to estimate the illumination and then set camera or flash parameters. Our method offers real time estimates of illumination at multiple locations, including correction terms such as orientation and reflectance.

Camera Adaptation and Factorization

Optimal camera parameters can be estimated by taking readings from the tags. Typically, conventional cameras use 'onboard' light meters to estimate, for instance, focus and exposure duration settings. However, it is difficult for on-board sensors to produce useful estimates when the scene is constantly changing or the camera is moving.

With several light sensors wirelessly transmitting information regarding irradiance and location, such parameter settings can be made more accurately and with added functionality. For example, the focus or gain for a current image or frame acquired by an automatic camera are determined from a recently acquired previous image or frame.

Because the tags in our system are fixed in world coordinates rather than camera coordinates, the tags can provide appropriate scene data even before the camera acquires any frame. In addition, given irradiance versus reflectance estimates, it is possible to select appropriate spatially varying gain to capture an albedo-image rather than a radiance-image. A reflectance-illumination factorization of camera images opens up many opportunities in computer and machine vision.

In one embodiment of the invention, an intrinsic reflectance of objects is determined. Photo sensors, in the form of the tags 200 are arranged in a scene, as shown in FIG. 1. Photometric and geometric attributes are acquired by the tags. The photometric attributes can be parameterized according to wavelength, amplitude, phase, polarization, phospherence, fluorescence, angle and combinations thereof.

An image of the scene is also acquired. The pixel values in the image are divided by the appropriate photo sensor reading, e.g., photo current, this is fine because it says 'e.g.' (for example) to determine the true reflectance. As those skilled in the art will recognize, a variety of electronic signals could be used for photo sensor readings, such as, but not limited to, photo current or voltage current. The division by the photo sensor reading is effectively a normalization that cancels the effect of incident light. Thus, a gray surface can be detected as specific value of gray independent of whether the surface is illuminated with bright light or dim light.

It is also possible to set parameters of a camera using information from the photo sensors. Conventional automatic cameras set their parameters, e.g., exposure and focus, according to on-board sensors. In an embodiment of the invention, the pixel values in an image acquired by the camera are divided by the data sensed by the tags to determine the camera parameters. The camera parameters can also include aperture, sensor gain, white balance, color filters, polarization filters, anti-blooming, anti-ghosting, and combinations thereof.

Improved Communication

Our choice of time division multiplexing is driven by availability of low cost off-the-shelf IR sensors and programmable microcontrollers. However, our system is scalable. In tests, we have shown that we can achieve very high ID update rates using transceivers intended for use with IrDA communication. We can operate the system at 250 Kbits per second, which means an effective frame rate of 20,000 frames per second for a single axis. We can also use optical FDMA or CDMA for 'always on' space labeling that does not require temporal synchronization.

Spatially Coded Light Sources

We can use a dense array of emitters to simplify decoding of the tags along orthogonal directions. It is also possible to use a disorganized set of emitters that are randomly distributed in environment. For some applications, a low resolution is sufficient, e.g., in more casual environments of home or office. When high resolution is desired, such as for industrial or motion capture applications, the number of emitters can be increased.

EFFECT OF THE INVENTION

In the near future, light sources used in movie studios, television sets, conference rooms, offices and even homes will be based on solid-state technology. These fast-switching light sources naturally lend themselves to applications beyond simple illumination. The invention provides a scheme in which a modern solid-state light source can be employed to estimate useful parameters related to locations in the environment, both geometric (location, orientation) as well as photometric (incident intensity, incident spectrum, surface reflectance). The spatio-temporal coded projection of light that we have described is a powerful way to label 2D or 3D space because fast switching light emission is one of the simplest forms of optical transmission.

The invention uses spatio-temporal modulation that exploits the epipolar geometry of a carefully configured cluster of light emitters to determine locations of optical tags in a 3D scene. Because the optical light sensed at any location in a scene is unique, we essentially have a space labeling projection of the light.

The invention can use an intensity-based technique for determining the orientation of the tags, a feature not available in most prior art optical markers.

The invention provides a simple method to determine the intrinsic reflectance of each scene location by sensing its irradiance and factorizing radiance measured by a camera.

In motion capture applications, the invention facilitates the use of imperceptible markers that can be integrated with an actor's desired costume and shot under natural or theatrical lighting conditions. Unlike conventional markers, the tags also provide photometric attributes. The invention provides methods for supporting graphics/vision applications that exploit both geometric and photometric sensed quantities.

One advantage of the invention is that it is based on components developed by the rapidly advancing fields of optical communication and solid-state lighting and sensing. In addition, the invention enables one to capture photometric quantities without added software or hardware overhead. Conventional tag-based techniques that use other physical media cannot capture photometric attributes.

Because the photo sensors are barely discernible, the characters can wear natural clothing with the photo sensing element of the tag poking out of the clothing. The ambient lighting can also be natural because the photo sensors receive well-powered IR light. The power is comparable to IR emission from TV remote controls. So, in studio settings, the actor may wear the final costume, and can be shot under theatrical lighting.

The bandwidth efficiency is the ratio of useful pixels in a frame to the total number of pixels. For an n×n image at f frames per second observing k tags, the efficiency is (f×k)/(f×n2)=k/2n with f updates per second. The efficiency is (f/2)/(f×n)=1/2n with f/k updates per second and hence such a system is ideally suited for high-speed tracking of a small number of markers. By using continuously streaming beamers and an unlimited number of photo sensing markers (or tags), the number of useful pixels (single pixel photo sensor on each of the k tags) and total number of pixels (k tags) become equal, yielding the maximum bandwidth efficiency.

Our approach greatly simplifies this problem by using probes (tags) at the scene locations of interest to directly sample location, orientation, and irradiance. We sample physically at scene locations. We solve the correspondence problem over successive frames via assigned tag IDs. Hence, we can analyze the history of the geometric and photometric parameters computed for a tag even when the scene location leaves the camera's field of view. Furthermore, our scene parameters are updated much faster than possible at a camera frame-rate. Therefore, we are able to demonstrate new video manipulation capabilities that are not possible by using the video alone.

We achieve functionality similar to multiplexed radio frequency (RF) communication by constructing 'always on' emitters. The data are transmitted without synchronization and without prior knowledge of tag locations. The optical spectrum has the added attributes that the signal is directional, its strength is dependent on receiver orientation and its interaction can be sampled by an external observer (camera) at a lower frame rate.

Similar to radio frequencies, for transmitting multiple signals to a single receiver, we can select to modulate light by multiplexing and demultiplexing amplitude, frequency, polarization, phase, time-division, code or combinations thereof. We can also use polarization and wavelength. Our use of passive binary spatial masks in a strategic configuration exploits epipolar constraints results in a system that is effective and yet simple.

Although the invention has been described by way of examples of preferred embodiments, it is to be understood that various other adaptations and modifications can be made within the spirit and scope of the invention. Therefore, it is the object of the appended claims to cover all such variations and modifications as come within the true spirit and scope of the invention.

We claim:

1. An apparatus arranged at a location in a scene, comprising:
   a photo sensor arranged at the location in the scene and configured to detect spatio-temporal modulated optical signals directed at the scene from a set of spatially dispersed optical transmitters, and to convert the optical signals from each of the optical transmitters to a corresponding electronic signal, wherein an encoding of the spatio-temporal modulated signals exploit an epipolar geometric relationship between the spatially dispersed optical transmitters and the photo sensor, and wherein the photo sensor is a single photo diode; and wherein a passive binary mask in front of each of the optical transmitters encodes the spatio-temporal modulated optical signals; and
   a means, connected to the photo sensor, for analyzing values of the electronic signals to determine geometric properties of the location in the scene.

2. The apparatus of claim 1, in which the geometric properties include three-dimensional coordinates of the location and a three dimensional orientation at the location in the scene.

3. The apparatus of claim 1, in which the geometric properties include a six-dimensional pose, wherein the pose specifies a 3D location and a 3D orientation.

4. The apparatus of claim 1, in which the geometric properties include a rate of change of coordinates of the location and a rate of change of an orientation of the location.

5. The apparatus of claim 1, in which the optical signals are multiplexed.

6. The apparatus of claim 1, in which the optical signals have frequencies that are selected from the group consisting of ultraviolet, visible, near-infrared and far-infrared light.

7. The apparatus r of claim 1, in which the optical light is modulated according to modulation selected from the group consisting of amplitude, time, wavelength, frequency, code, phase, and polarization modulation.

8. The apparatus of claim 1, in which the optical signal is unique at all locations in the scene to generate a space labeling projection.

9. The apparatus of claim 1, further comprising:
   means for transmitting the geometric properties.

10. The apparatus of claim 1, in which the optical receiver includes an radio frequency identification tag.

11. The apparatus of claim 1, in which the optical receiver is mounted on a moving object.

12. The apparatus of claim 1, further comprising:
means for transceiving with optical communication signals.

13. The apparatus of claim 1, in which a wavelength of the optical signals is in a range of about 0.01 to 1000 micrometers.

14. The apparatus of claim 2, in which the three dimensional orientation at the location in the scene is determined by measuring a cosine falloff of the optical signals as the photo sensor is tilted.

15. The apparatus of claim 1, further comprising:

measuring a reflectance in the scene.

16. The apparatus of claim 1, further comprising:

means for setting parameters of a camera according to the detected optical signals.

* * * * *